United States Patent
Patel

(10) Patent No.: US 8,937,081 B2
(45) Date of Patent: Jan. 20, 2015

(54) STATIN BIOAVAILABILITY ENHANCEMENT DELIVERY COMPOSITION

(71) Applicant: PruGen IP Holdings, Inc., Scottsdale, AZ (US)

(72) Inventor: Bhiku G. Patel, Chandler, AZ (US)

(73) Assignee: PruGen IP Holdings, Inc., Scottsdale, AZ (US)

( * ) Notice: Subject to any disclaimer, the term of this patent is extended or adjusted under 35 U.S.C. 154(b) by 0 days.

(21) Appl. No.: 13/712,847

(22) Filed: Dec. 12, 2012

(65) Prior Publication Data

US 2013/0150393 A1 Jun. 13, 2013

Related U.S. Application Data

(60) Provisional application No. 61/569,697, filed on Dec. 12, 2011.

(51) Int. Cl.
| | |
|---|---|
| *A61K 47/00* | (2006.01) |
| *A61K 47/10* | (2006.01) |
| *A61K 47/44* | (2006.01) |
| *A61K 47/26* | (2006.01) |
| *A61K 47/22* | (2006.01) |

(52) U.S. Cl.
CPC ............... *A61K 47/00* (2013.01); *A61K 47/26* (2013.01); *A61K 47/22* (2013.01); *A61K 47/44* (2013.01); *A61K 47/10* (2013.01)
USPC .......................................................... 514/275

(58) Field of Classification Search
None
See application file for complete search history.

(56) References Cited

U.S. PATENT DOCUMENTS

| | | |
|---|---|---|
| 2002/0040046 A1 | 4/2002 | Patel et al. |
| 2003/0171264 A1 | 9/2003 | Naicker et al. |
| 2004/0235935 A1 | 11/2004 | Vanderbist et al. |
| 2005/0191343 A1 | 9/2005 | Liang |
| 2006/0165769 A1 * | 7/2006 | Hyatt et al. .................. 424/450 |
| 2008/0213378 A1 | 9/2008 | Cooper et al. |

FOREIGN PATENT DOCUMENTS

| | | | |
|---|---|---|---|
| WO | WO 2009084040 A1 * | 7/2009 | |
| WO | WO 2010098906 A1 * | 9/2010 | |

OTHER PUBLICATIONS

The Dow Chemical Company, http://www.dow.com/polyglycols/ppgc/europe/products/ppg.htm.*
Ke et al., "Physical characterizations of microemulsion systems using tocopheryl polyethylene glycol 1000 succinate (TIPGS) as a surfactant for the oral delivery of protein drugs," Feb. 2, 2005, vol. 102, No. 2, pp. 489-507.
PCT/US2012/069301—International Search Report and Written Opinion dated Mar. 15, 2013.
PCT/US2012/069301—International Preliminary Report on Patentability dated Jun. 26, 2014.

* cited by examiner

*Primary Examiner* — Melenie McCormick
*Assistant Examiner* — Taina D Matos Negron
(74) *Attorney, Agent, or Firm* — Dale F. Regelman; Quarles & Brady LLP

(57) ABSTRACT

A composition for increasing the bioavailability of a statin active pharmaceutical ingredient ("API") in humans and animals, wherein that composition includes a statin API selected from the group consisting of atorvastatin, fluvastatin, lovastatin, pitavastatin, pravastatin, rosuvastatin, and simvastatin, a first water soluble surfactant having a cloud point greater than about 37° C., a second water soluble surfactant having a cloud point greater than about 37° C., wherein a mixture of the first surfactant and the second surfactant comprises a cloud point less than about 37° C.

4 Claims, 1 Drawing Sheet

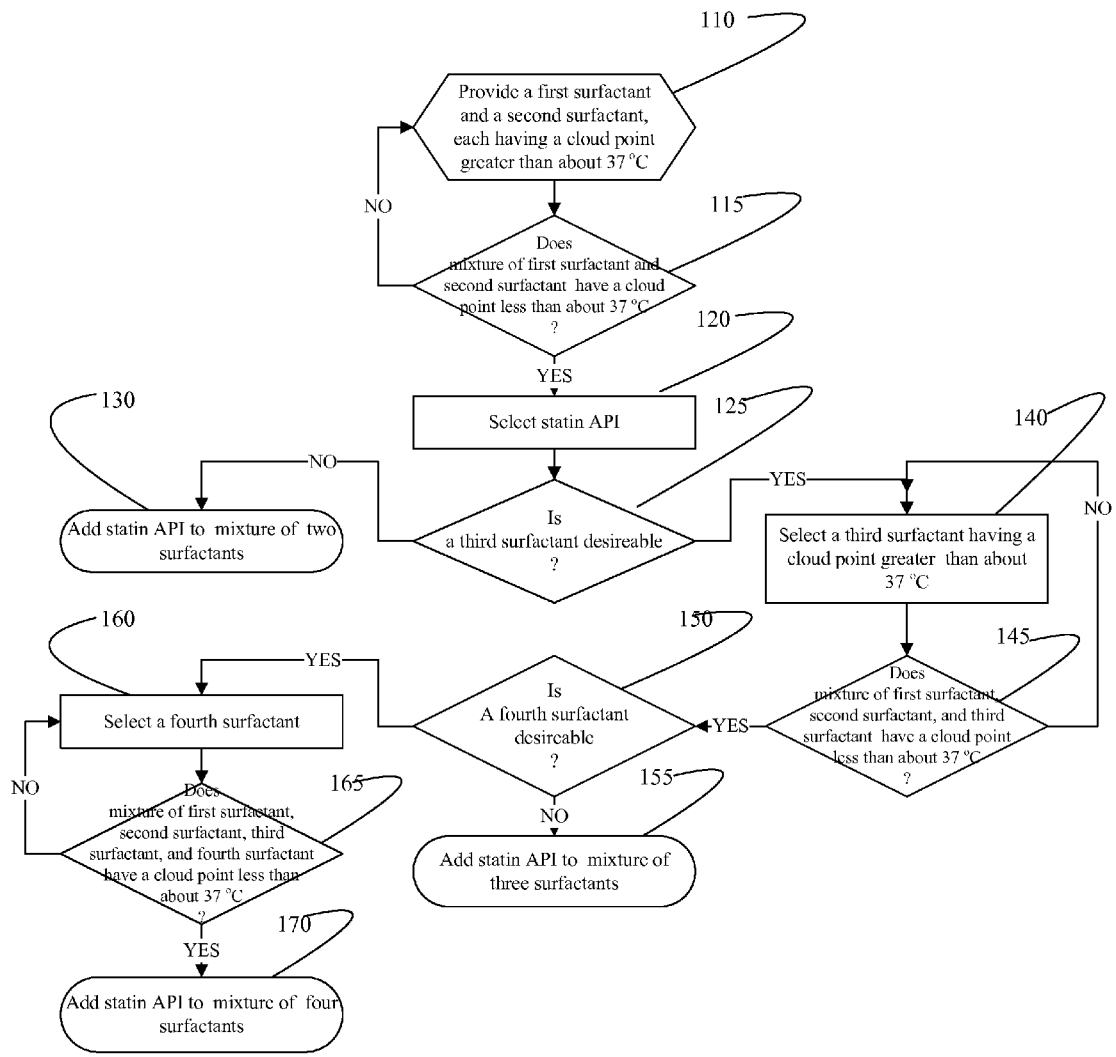

STATIN BIOAVAILABILITY ENHANCEMENT DELIVERY COMPOSITION

CROSS-REFERENCE TO RELATED APPLICATION

This Non-Provisional Application claims priority to U.S. Provisional Application having Ser. No. 61/569,697, filed on Dec. 12, 2011, and which is hereby incorporated by reference herein.

TECHNICAL FIELD

The present invention relates to the solubilization of statin drugs and more particularly to a composition for solubilizing statin drugs in a plurality of non-ionic surfactants and a method for forming same.

BACKGROUND ART AND PRIOR ART

HMG-CoA reductase inhibitors, more commonly known as statins, are a class of drugs used to lower cholesterol levels. They are reported to work by inhibiting the enzyme HMG-CoA reductase, which plays a central role in the production of cholesterol in the liver. Hypercholesterolemia is considered to be one of the major risk factors for atherosclerosis which often leads to cardiovascular, cerebrovascular and peripheral vascular diseases. The statins inhibit cholesterol synthesis in the body and that leads to reduction in blood cholesterol levels, which is thought to reduce the risk of atherosclerosis and diseases caused by it.

The best-selling statin drug is atorvastatin, marketed as LIPITOR and manufactured by Pfizer. A number of other statins are also currently on the market: fluvastatin, lovastatin, pitavastatin, pravastatin, rosuvastatin, and simvastatin.

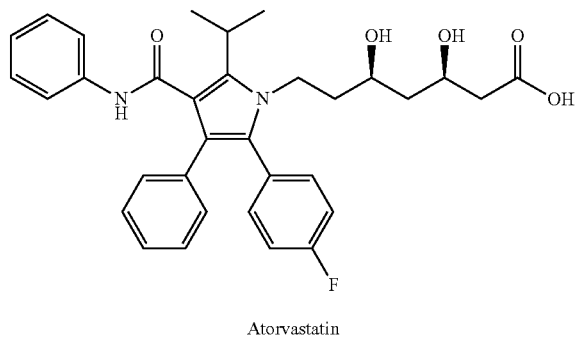 [SMILES: CC(C)c1c(C(=O)Nc2ccccc2)c(-c2ccccc2)c(-c2ccc(F)cc2)n1CC[C@@H](O)C[C@@H](O)CC(=O)O]

Atorvastatin

While atorvastatin has been shown in numerous studies to be an effective cholesterol-lowering and low density lipoprotein uptake reducing drug, it is not without its shortcomings. Among these shortcomings, atorvastatin has low bioavailability after oral administration and a high number of perceived side effects. The absolute bioavailability of atorvastatin is approximately 14% which is thought to be the result of two major factors: atorvastatin undergoes high intestinal clearance and first-pass metabolism and, importantly it is insoluble in aqueous solution. Side effects include, among others, the potential for causing liver and muscle disease. This is the result of increased load requirements secondary to atorvastatin's low systemic availability.

BRIEF DESCRIPTION OF THE DRAWINGS

The invention will be better understood from a reading of the following detailed description taken in conjunction with the drawings in which like reference designators are used to designate like elements, and in which:

FIG. 1 is a flow chart summarizing the steps of Applicant's method.

DETAILED DESCRIPTION OF THE PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagram included herein is generally set forth as logical flow-chart diagram (e.g., FIG. 1). As such, the depicted order and labeled steps are indicative of one embodiment of a presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

There is need for a composition to solubilize atorvastatin, and other statin APIs, in a non-ionic environment that enhances dispersion and absorption which positively impacts intestinal clearance and bioavailability of statin drugs. By "statin APIs," and "statin drugs," Applicant means non ionized Type 1 and Type 2 statin medicaments, and pharmaceutically effective salts thereof, including without limitation sodium salts, potassium salts, calcium salts, and organic salts such as ammonium salts and the like. The present invention presents such a composition.

As a general matter, any active pharmaceutical ingredient ("API"), whether a weak acid or a weak base, and its pKa determine the extent of ionization according to the pH partition hypothesis at various pH values (pH 1.3 for stomach and 6 for intestine) of the gastrointestinal tract. Drugs that are not ionized or that undergo hydrogen bonding exhibit a much greater lipophilicity toward membrane permeation than their ionic counterparts. Lipophilicity is, a major determinant for predicting the extent of membrane permeation.

Lipophilicity of the statins is considered to be quite important since the hepatoselectivity of the statins is related to their lipophilicity. The more lipophilic statins tend to achieve higher levels of exposure in non-hepatic tissues, while the hydrophilic statins tend to be more hepatoselective. The difference in selectivity is because lipophilic statins passively and non-selectively diffuse into both hepatocyte and non-heptatocyte, while the hydrophilic statins rely largely on active transport into hepatocyte to exert their effects.

High hepatoselectivity is thought to translate into reduced risk of adverse effects. It has been reported that the organic anion transporting polypeptide (OATP) is important for the hepatic uptake of hydrophilic statins such as rosuvastatin and pravastatin. OATP-C is expressed in liver tissue on the basolateral membrane of hepatocytes and is considered to be a potential contributor for the low IC50 for rosuvastatin in hepatocytes. Of the marketed statins, cerivastatin was the most lipophilic and also had the largest percentage of serious adverse effects due to its ability to inhibit vascular smooth muscle proliferation and as a result was voluntarily removed from the market by the manufacturer.

Statins have sometimes been grouped into two groups of statins according to their structure. Type 1 statins comprise substituted decalin-ring structure that resemble the first statin ever discovered, mevastatin. Statins that belong to this group include Lovastatin, Pravastatin, and Simvastatin.

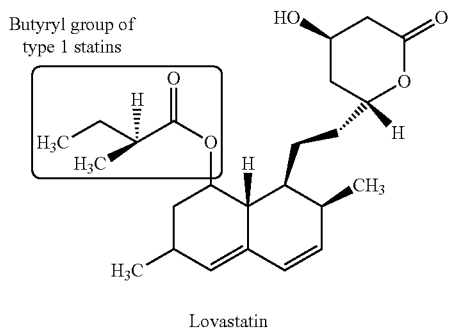

Lovastatin

Type 2 statins are fully synthetic and have larger groups linked to the HMG-like moiety. One of the main differences between the type 1 and type 2 statins is the replacement of the butyryl group of type 1 statins by the fluorophenyl group of type 2 statins. This group is responsible for additional polar interactions that causes tighter binding to the HMGR enzyme. Statins that belong to this group include Fluvastatin, Cerivastatin, Atorvastatin, and Rosuvastatin.

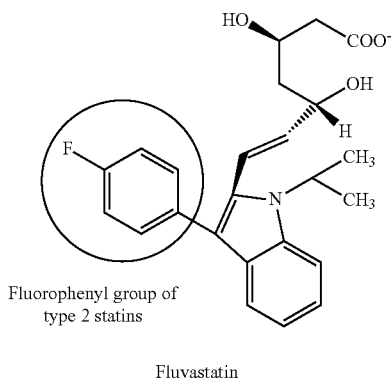

Fluvastatin

Applicants' statin bioavailability enhancement delivery composition addresses the problem of statin bioavailability. Certain prior art pharmaceutical compositions comprise emulsions. Broadly speaking, an emulsion is a mixture of two or more immiscible liquids. Prior art drug delivery emulsion attempts have focused on macroemulsions comprising a plurality of API droplets disposed within a continuous aqueous phase. These prior art drug delivery compositions and methods also require heat and the input of considerable amounts of mechanical energy, which may be supplied by colloid mills, homogenizers, and ultrasonic generators. This raises the cost of preparation in a potentially less than desirable product.

Cloud point is the temperature above which an aqueous solution of a water-soluble surfactant becomes turbid. Generally, nonionic surfactants show optimal effectiveness when used near or below their cloud point.

Cloud points are typically measured using 1% aqueous surfactant solutions. Cloud points range from 0° to 100° C. (32 to 212° F.), limited by the freezing and boiling points of water. Cloud points are characteristic of nonionic surfactants. Anionic surfactants (with negatively charged groups) are more water-soluble than nonionic surfactants and will typically have much higher cloud points (above 100° C.). The presence of other components in a formulation can depress or increase the solution's cloud point.

Cloud point is also a measure of the hydrophilic/lipophilic balance of a surface-active agent. When a surfactant can have its cloud point run in an aqueous solution, it is therefore a water soluble surface active agent; whereas, when a surfactant must have its cloud point run in an aqueous/solvent mixture, it is either water dispersible or oil soluble in character. Nonionic surface-active agents are less soluble at elevated temperatures in aqueous solutions and, therefore, exhibit a cloud point which varies with the hydrophilic/lipophilic balance of the nonionic surface-active agent.

In certain embodiments, Applicants' statin bioavailability enhancement delivery composition comprises a first surfactant and a second surfactant. In certain embodiments, the first surfactant comprises a cloud point greater than about 37° C. In certain embodiments, the second surfactant comprises a cloud point greater than about 37° C. In certain embodiments, both the first surfactant and the second surfactant individually comprise cloud points greater than about 37° C. In certain embodiments, the first surfactant comprises a HLB between about 14 and about 16. In certain embodiments, the second surfactant comprises a HLB between about 14 and about 16. In certain embodiments, both the first surfactant and the second surfactant individually comprises a HLB between about 14 and about 16.

In certain embodiments, Applicant's first surfactant comprises an ethoxylated carbohydrate moiety. In certain embodiments, Applicant's first surfactant comprises structure I, wherein a, b, c, d, e, and f, are independently between 0 and about 20. R1, R2, R3, R4, R5, and R6, are selected from the group consisting of H and —CO—R7, wherein R7-COOH comprises a fatty acid. In certain embodiments, R7-COOH is selected from the group consisting of Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, and Docosahexaenoic acid.

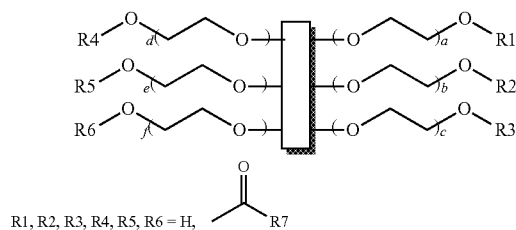

I

R1, R2, R3, R4, R5, R6 = H,

Sorbitol, also known as glucitol, SORBOGEM and SORBO, is a sugar alcohol that the human body metabolizes slowly. It can be obtained by reduction of glucose, changing the aldehyde group to a hydroxyl group. Sorbitol is found in apples, pears, peaches, and prunes.

Sorbitan is a mixture of chemical compounds derived from the dehydration of sorbitol. The mixture can vary, but usually consists of 1,4-anhydrosorbitol, 1,5-anhydrosorbitol and 1,4,3,6-dianhydrosorbitol. Sorbitan is primarily used in the production of surfactants such as polysorbates.

Sorbitan esters (also known as Spans) are lipophilic non ionic surfactants that are used as emulsifying agents in the preparation of emulsions, creams, and ointments for pharmaceutical and cosmetic use. When used alone they produce stable water-in-oil emulsions but they are frequently used with a polysorbate in varying proportions to produce water-in-oil or oil-in-water emulsions or creams with a variety of different textures and consistencies. Sorbitan esters are also used as emulsifiers and stabilizers in food In certain embodiments, Applicant's first surfactant comprises a carbohydrate moiety. In certain embodiments, Applicant's first surfactant comprises a polysorbate having structure II, wherein w is between about 1 to about 20 and wherein x, y, and z, are each between 0 to about 20, and wherein R7 is defined hereinabove.

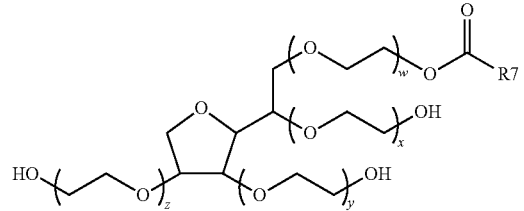

In certain embodiments, Applicant's first surfactant comprises polyoxyethylene sorbitan monooleate III.

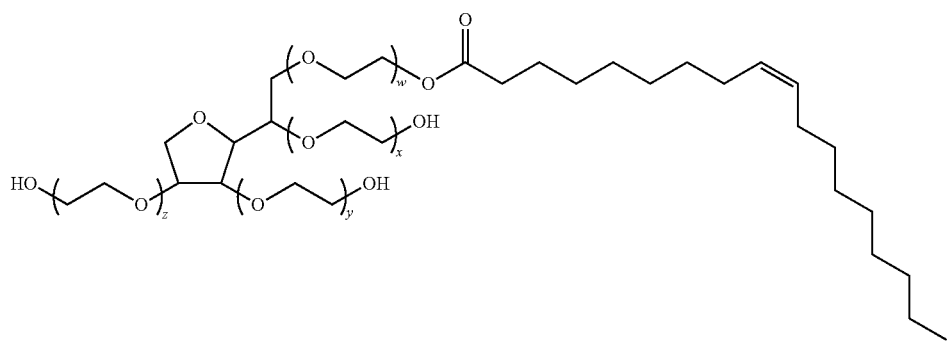

$w + x + y + z = 20$

Compound III comprises an average molecular weight of about 1310, a micellar average molecular weight of about 79,900, an aggregation number of about 60, a cloud point of about 65° C., and a HLB of about 15.

In certain embodiments, Applicant's second surfactant comprises a vitamin moiety. In certain embodiments, Applicant's second surfactant comprises an ethoxylated vitamin composition. In certain embodiments, Applicant's second surfactant comprises an esterified Vitamin E composition. In certain embodiments, Applicant's second surfactant comprises tocopheryl polyethylene glycol succinate IV, wherein n is between about 10 to about 100.

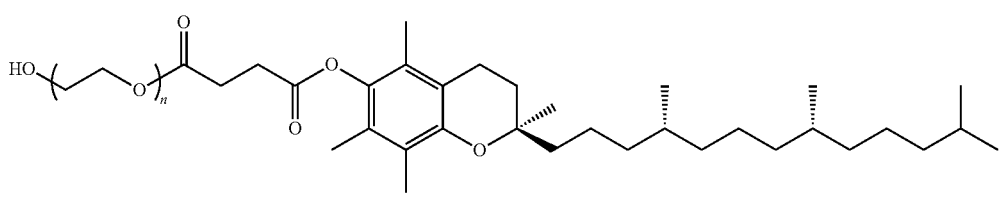

Tocopheryl polyethylene glycol succinate comprises a cloud point of between 62° C. and about 75° C. at concentrations of from about 0.05 weight percent to about 15 weight percent, respectively. Tocopheryl polyethylene glycol succinate comprises a HLB of about 13.

In certain embodiments, Applicants' statin bioavailability enhancement delivery composition comprises a first surfactant comprising a cloud point greater than about 37° C., and a second surfactant comprising a cloud point greater than about 37° C., wherein a mixture of the first surfactant and the second surfactant comprises a cloud point less than 37° C.

Surfactant molecules self-associate in dilute aqueous solutions to generate aggregates of various types, shapes, and sizes such as small globular micelles, large cylindrical micelles, and spherical vesicles. The characteristics of the aggregates formed are determined by the molecular structure of the surfactant as well as by the solution conditions such as concentration, temperature, ionic strength, and the like.

In certain embodiments, the second surfactant enhances the ability of the first surfactant to form micelles in water. In certain embodiments, the first surfactant comprises a first critical micelle concentration, wherein the combination of the first surfactant and the second surfactant comprises a second critical micelle concentration, wherein the second critical micelle concentration is less than the first critical micelle concentration. In certain embodiments, the first surfactant comprises a first critical micelle temperature, wherein the combination of the first surfactant and the second surfactant comprises a second critical micelle temperature, wherein the second critical micelle temperature is less than the first critical micelle temperature.

In certain embodiments, the first surfactant forms a first micelle comprising a first micellar average molecular weight. The combination of the first surfactant and the second surfactant forms a mixed micelle comprising a mixed micellar average molecular weight, wherein the first micellar average molecular weight differs from the mixed micellar average molecule weight.

In certain embodiments, Applicants' statin bioavailability enhancement delivery composition further comprises a third surfactant. In certain embodiments, Applicant's third surfactant comprises a cloud point greater than about 37° C. In certain embodiments, Applicant's bioavailability enhancement delivery composition comprises a first surfactant comprising a cloud point greater than about 37° C., a second surfactant comprising a cloud point greater than about 37° C., and a third surfactant comprising a cloud point greater than about 37° C., wherein a mixture of the first surfactant, the second surfactant, and the third surfactant comprises a cloud point less than 37° C.

In certain embodiments, Applicant's third surfactant comprises a triglyceride moiety. In certain embodiments, Applicant's third surfactant comprises an ethoxylated triglyceride. In certain embodiments, Applicant's third surfactant comprises ethoxylated castor oil V.

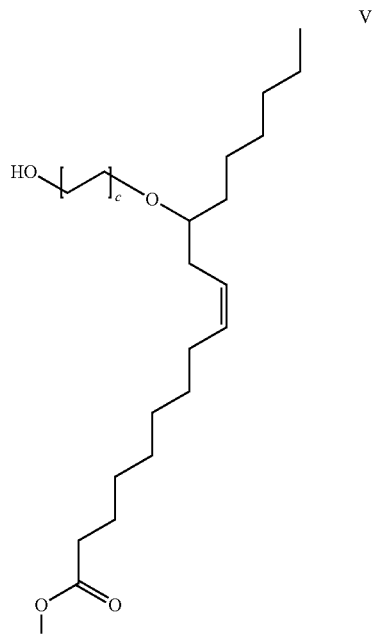

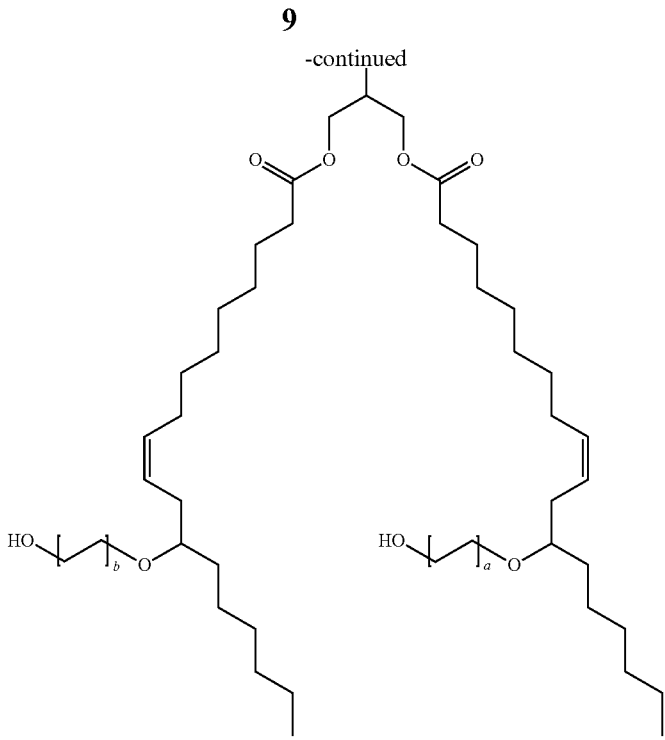

The reaction product of castor oil and about 30 equivalents of ethylene oxide, i.e. a+b+c=30, comprises a cloud point of about 73° C. (1% in 20% acetic acid). The reaction products of castor oil and between about 30 equivalents to about 60 equivalents of ethylene oxide comprise HLB values of between about 12 to about 15.

Treating castor oil with an excess of ethylene oxide forms a plurality of other compounds in addition to adduct V. Minor components are the polyethylene glycol esters of ricinoleic acid, polyethylene glycols and polyethylene glycol ethers of glycerol. In certain embodiments, Applicant's bioavailability enhancement delivery composition comprises polyethylene glycol esters of various fatty acids, including ricinoleic acid, polyethylene glycols and polyethylene glycol ethers of glycerol.

In certain embodiments, Applicants' statin bioavailability enhancement delivery composition comprises a fourth surfactant. In certain embodiments, Applicant's fourth surfactant comprises a polyoxylglyceride. Polyoxylglycerides are mixtures of monoesters, diesters, and triesters of glycerol and monooesters and diesters of polyethylene glycols. These mixture are produced by partial alcoholysis of triglycerides of one or more fatty acids, such as and without limitation oleic acid, lauric acid, stearic acid, and the like, by esterification of glycerol and polyethylene glycols with fatty acids, or as a mixture of glycerol esters and ethylene oxide condensate with the fatty acids of the hydrogenated oils.

In certain embodiments, the third surfactant and the fourth surfactant are added in a weight ratio range of about 1:1 to about 1:12 with a 1:1 mixture being optimal. When measured with respect to the statin API alone, the statin API/third and fourth surfactant mixture weight ratio is from about 1:10 to about 1:26 with a ratio of about 1:20 being optimal for divalent drug salts and about 1:15 for monovalent drug salts.

In certain embodiments, a weight ratio of a mixture of the first surfactant and the second surfactant to a mixture of the third surfactant and the fourth surfactant, without taking into account the amount of a statin API, is from about 1:15 to about 1:30. At these ratios, Applicants' statin bioavailability enhancement delivery composition comprises a clear solution that does not formed a precipitate upon standing at room temperature.

FIG. 1 summarizes Applicant's method to prepare Applicants' statin bioavailability enhancement delivery composition. Referring to FIG. 1, in step 110 the method provides a first surfactant and a second surfactant. In certain embodiments, the first surfactant comprises a cloud point greater than about 37° C. In certain embodiments, the first surfactant comprises a HLB value in the range of about 12 to about 18. In certain embodiments, the first surfactant comprises a first critical micelle concentration. In certain embodiments, the first surfactant comprises a first critical micelle temperature. In certain embodiments, the first surfactant comprises polyoxyethylene sorbitan monooleate.

In certain embodiments, the second surfactant comprises a cloud point greater than about 37° C. In certain embodiments, the first surfactant comprises a HLB value in the range of about 12 to about 18. In certain embodiments, the second surfactant comprises tocopheryl polyethylene glycol succinate.

In step 115, the method determines if a mixture of the first surfactant and the second surfactant comprises a cloud point less than about 37° C. If the method determines in step 115 that a mixture of the first surfactant and the second surfactant does not comprise a cloud point less than about 37° C., then the method transitions from step 115 to step 110 and continues as described herein.

If the method determines in step 115 that a mixture of the first surfactant and the second surfactant does comprise a cloud point less than about 37° C., then the method transitions from step 115 to step 120 wherein the method selects an active statin pharmaceutical ingredient ("API"). In certain embodiments, the statin API of step 120 is selected from the group consisting of atorvastatin, fluvastatin, lovastatin, pitavastatin, pravastatin, rosuvastatin, and simvastatin.

In step 125, the method determines if a third surfactant is desirable. In certain embodiments, step 125 includes determining the solubility of the selected statin API of step 120 in the mixture of surfactants of step 110. In certain embodiments, step 125 includes varying the weight ratio of the first surfactant to the second surfactant. In certain embodiments, the weight ratio of the first surfactant to the second surfactant is about 4:1. In certain embodiments, the weight ratio of the first surfactant to the second surfactant is about 2:1. In certain embodiments, step 125 includes determining a pharmaceutically effective dosage of the statin API selected in step 120.

If the method determines in step 125 that a third surfactant is not desirable, then the method transitions from step 125 to step 130 wherein the method forms Applicant's statin bioavailability enhancement delivery composition by adding a pharmaceutically effective dosage of the statin API selected in step 120 to a mixture of the first surfactant and second surfactant of step 110.

If the method determines in step 125 that a third surfactant is desirable, then the method transitions from step 125 to step 140 wherein the method selects a third surfactant. In certain embodiments, the third surfactant comprises a cloud point greater than about 37° C. In certain embodiments, the third surfactant comprises a HLB value in the range of about 12 to about 18. In certain embodiments, the third surfactant comprises ethoxylated castor oil.

In step 145, the method determines if a mixture of the first surfactant, second surfactant, and third surfactant comprises a cloud point less than about 37° C. If the method determines in step 145 that a mixture of the first surfactant, second surfactant, and third surfactant does not comprise a cloud point less than about 37° C., then the method transitions from step 145 to step 140 and continues as described herein. If the method determines in step 145 that a mixture of the first surfactant, second surfactant, and third surfactant does comprise a cloud point less than about 37° C., then the method transitions from step 145 to step 150, wherein the method determines if a fourth surfactant is desirable.

If the method determines in step 150 that a fourth surfactant is not desirable, then the method transitions from step 150 to step 155 wherein the method forms Applicant's statin bioavailability enhancement delivery composition by adding a pharmaceutically effective dosage of the statin API selected in step 120 to a mixture of the first surfactant and second surfactant of step 110, and the third surfactant of step 140.

If the method determines in step 150 that a fourth surfactant is desirable, then the method transitions from step 150 to step 160 wherein the method selects a fourth surfactant. In step 165, the method determines if a mixture of the first surfactant, second surfactant, third surfactant, and fourth surfactant, comprises a cloud point less than about 37° C. If the method determines in step 165 that a mixture of the first surfactant, second surfactant, third surfactant, and fourth surfactant does not comprise a cloud point less than about 37° C., then the method transitions from step 165 to step 160 and continues as described herein.

In certain embodiments, the fourth surfactant comprises a 400 Dalton polypropylene glycol having a cloud point in a 1 weight percent aqueous solution of greater than about 95° C. In certain embodiments, the fourth surfactant comprises a 600 Dalton polypropylene glycol having a cloud point in a 1 weight percent aqueous solution of greater than about 65° C.

If the method determines in step 165 that a mixture of the first surfactant, second surfactant, third surfactant, and fourth surfactant, does comprise a cloud point less than about 37° C., then the method transitions from step 165 to step 170 wherein the method forms Applicant's statin bioavailability enhancement delivery composition by adding a pharmaceutically effective dosage of the statin API selected in step 120 to a mixture of the first surfactant and second surfactant of step 110, and the third surfactant of step 140, and the fourth surfactant of step 160.

While the preferred embodiments of the present invention have been illustrated in detail, it should be apparent that modifications and adaptations to those embodiments may occur to one skilled in the art without departing from the scope of the present invention as set forth in the following claims.

I claim:

1. A composition for increasing the bioavailability of a statin active pharmaceutical ingredient ("API") in humans and animals, consisting of:
   a statin AP selected from the group consisting of atorvastatin, fluvastatin, lovastatin, pitavastatin, pravastatin, rosuvastatin, and simvastatin;
   polyoxyethylene sorbitan monooleate having a cloud point greater than about 37° C.;
   tocopheryl polyethylene glycol succinate having a cloud point greater than about 37° C.;
   wherein a mixture of said polyoxyethylene sorbitan monooleate and said tocopheryl polyethylene glycol succinate comprises a cloud point less than about 37° C.

2. The composition of claim 1, wherein a weight ratio of said polyoxyethylene sorbitan monooleate to said tocopheryl polyethylene glycol succinate is about 4:1.

3. The composition of claim 1, wherein a weight ratio of said polyoxyethylene sorbitan monooleate to said tocopheryl polyethylene glycol succinate is about 2:1.

4. A composition for increasing the bioavailability of a statin active pharmaceutical ingredient ("API") in humans and animals, consisting of:
   a statin API selected from the group consisting of atorvastatin, fluvastatin, lovastatin, pitavastatin, pravastatin, rosuvastatin, and simvastatin;
   polyoxyethylene sorbitan monooleate having a cloud point greater than about 37° C.;
   tocopheryl polyethylene glycol succinate having a cloud point greater than about 37° C.;
   ethoxylated castor oil;
   wherein a mixture of said polyoxyethylene sorbitan monooleate, said tocopheryl polyethylene glycol succinate, and said ethoxylated castor oil comprises a cloud point less than about 37° C.

* * * * *